United States Patent [19]

Lapointe et al.

[11] Patent Number: 5,105,805

[45] Date of Patent: Apr. 21, 1992

[54] HINGED KNEE BRACE ASSEMBLY

[75] Inventors: Warren C. Lapointe, Coventry; Louis J. Valois, Narragansett, both of R.I.

[73] Assignee: Quadrax Corporation, Portsmouth, R.I.

[21] Appl. No.: 546,445

[22] Filed: Jul. 3, 1990

[51] Int. Cl.⁵ .............................................. A61F 5/00
[52] U.S. Cl. ........................................ 602/16; 602/26
[58] Field of Search .................. 128/80 R, 80 C, 80 F, 128/80 H, 87 R, 88; 623/27, 39, 43, 47; 16/374, 377, 376; 403/117, 91–93

[56] References Cited

U.S. PATENT DOCUMENTS

| | | | |
|---|---|---|---|
| 3,881,522 | 5/1975 | Lewis et al. | 273/73 F |
| 4,153,052 | 5/1979 | Tsuk | 128/90 |
| 4,655,201 | 4/1987 | Pirmantgen | 128/80 C |
| 4,738,252 | 4/1988 | Friddle et al. | 128/80 H |
| 4,751,748 | 6/1988 | Ekins | 128/80 C |
| 4,929,113 | 5/1990 | Sheu | 403/91 |
| 5,005,565 | 4/1991 | Fratesi | |

Primary Examiner—Richard J. Apley
Assistant Examiner—Lynne Reichard
Attorney, Agent, or Firm—Fleit, Jacobson, Cohn, Price, Holman & Stern

[57] ABSTRACT

A hinged knee brace assembly includes upper and lower mounting members positionable above and below a wearer's knee, respectively. The mounting members include projecting connector link portions joined together along a transverse bending axis of the knee, on opposite sides thereof, by respective hinges. Each hinge comprises a stop plate member including a circumferentially extending track and a lug plate member having a projecting lug receivable in the track and engageable with stop surfaces at opposite ends thereof, to limit knee-bending movement. A first retaining member of each hinge has a noncircular projecting hub which projects through corresponding apertures in the lug plate member and the adjacent connector link portion of the lower mounting member to cause the lug plate member and connector link to move as a unit. Similarly, a second retaining member of each hinge causes the stop plate member and the adjacent connector link portion of the upper mounting member, and an associated outer plate member, to move as a unit. The parts at each hinged connection are connected together by a securing screw, the screw-threaded movement of which is limited to prevent clamping of the parts together so as to prevent the hinged connection from functioning properly. The upper mounting member includes a support member fixed thereto and having a lower free end, for insertion in a pocket of the wearer's clothing, to support the knee brace assembly on the wearer.

22 Claims, 2 Drawing Sheets

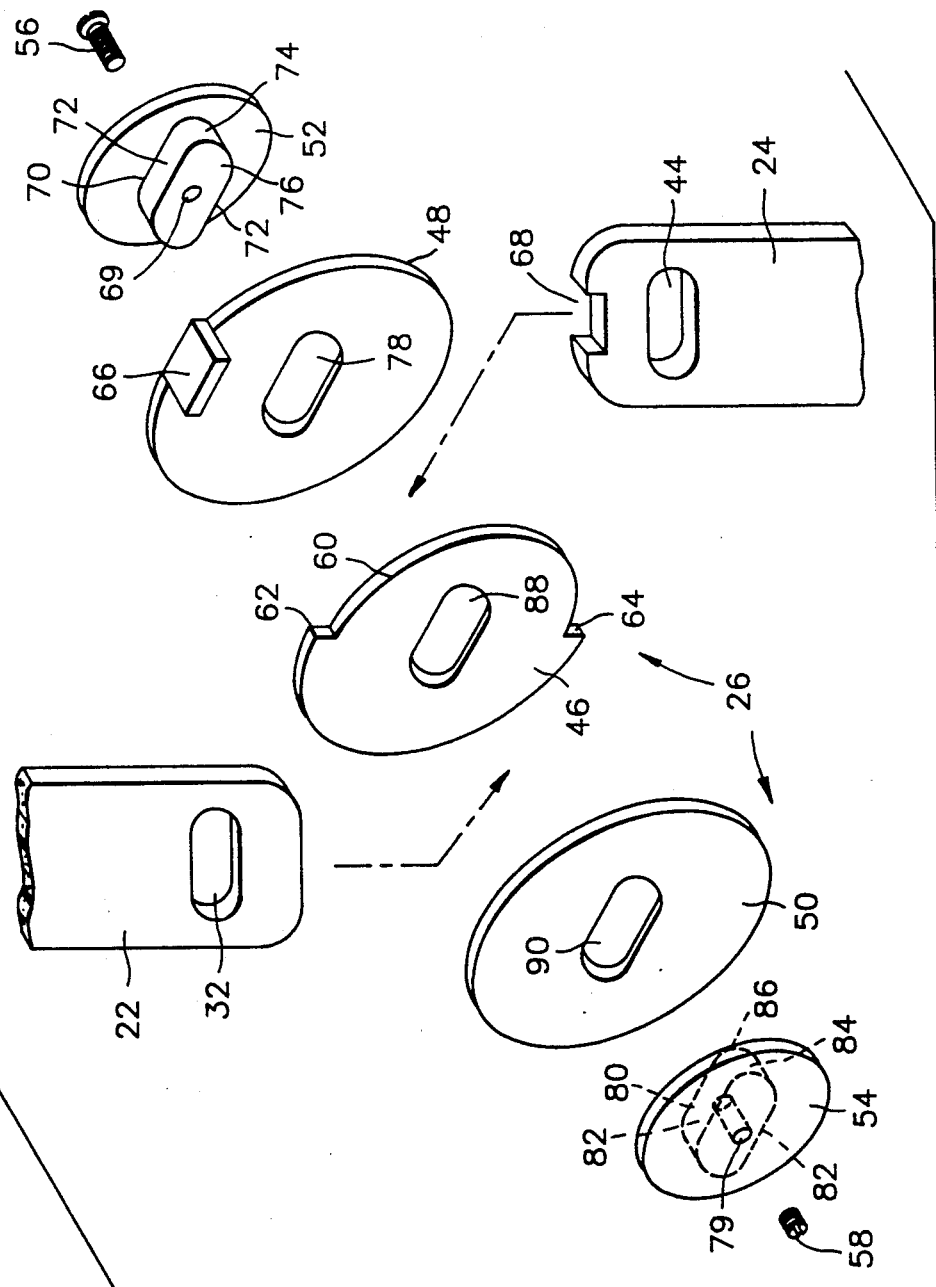

HINGED KNEE BRACE ASSEMBLY

1. Field of the Invention

This invention relates to a hinged knee brace assembly, and more particularly to a hinged knee brace assembly for preventing injury and possible permanent damage to a knee of a wearer, such as a professional athlete.

2. Description of the Related Art

Hinged knee braces for preventing injury to a wearer's knee and/or promoting healing of an injured knee, are known in the art. Typically, such a hinged knee brace may comprise an upper cuff member which is mounted to the wearer's thigh above the knee and a lower cuff member which is mounted to the wearer's calf below the knee. The upper cuff member may include downwardly projecting connector links, and the lower cuff member may include upwardly projecting connector links, with adjacent ends of the connector links pivotably interconnected by hinges on opposite sides thereof at a transverse bending axis of the knee. The hinged pivotable connections permit natural bending of the wearer's knee, but limit bending of the wearer's calf in an unnatural forward direction, which could cause ligament, cartilage or other damage to the knee. At the same time, the upper and lower cuff members, which may be mounted on the wearer's leg by suitable straps, cooperate with the hinges to prevent other unnatural bending of the knee which could cause damage thereto.

For example, a hinged knee brace assembly of this general type is disclosed in the J. H. Townsend U.S. Pat. No. 4,723,539. In that patent, each hinged connection between the upper and lower cuff members comprises camming slots formed in one of the connecting links, with cams disposed on the other connecting link. The camming slots comprise straight segments and arcuate segments so as to provide a selective degree of sliding movement between the wearer's femur and tibia, followed by relative rotation about the center of radius of the femoral condyle as the wearer's leg is flexed. Further, the lower cuff member is conformed about the bony prominence or shin of the wearer's tibia to inhibit rotation of the leg beneath the knee within the brace itself. Other prior art includes A. J. Gromes U.S. Pat. No. 1,336,695; M. Meierhofer U.S. Pat. No. 2,379,538; H. G. Gardner U.S. Pat. No. 3,779,158; R. V. Horne U.S. Pat. No. 3,779,654; G. A. Taylor U.S. Pat. No. 3,902,482; M. J. Almedia U.S. Pat. No. 4,139,002; D. T. Diebert U.S. Pat. No. 4,027,831; R. W Foster U.S. Pat. No. 4,353,361; and K. Buring, et al. U.S. Pat. No. 4,409,689.

However, a need still exists for a hinged knee brace assembly which is of simple, compact and rugged construction, and which is easy to assemble and mount on the wearer, and a primary purpose of this invention is to provide such a device.

SUMMARY OF THE INVENTION

In general, the subject invention includes a hinge for use with a knee brace assembly comprising first and second mounting members for mounting the knee brace assembly to a wearer's leg above and below a wearer's knee, respectively, with the hinge comprising a stop plate member adapted to be connected to one of the mounting members for movement therewith, and a lug plate member adapted to be connected to the other of the mounting members for movement therewith. The hinge also includes a pivot mechanism which pivotably interconnects the connected stop plate-mounting member, and the connected lug plate-mounting member, for relative pivotal movement. Further, the stop plate member includes a circumferentially extending track having stop surfaces at opposite ends thereof, and the lug plate member includes a projecting lug receivable in the circumferentially extending track of the stop plate member and selectively engageable with at least one of the stop surfaces of the track for limiting relative movement between the stop and lug plate members, and thus the mounting members.

More specifically, the hinge comprises a part of a knee brace assembly wherein the first mounting member includes spaced projecting connector link portions adapted to extend downward adjacent the wearer's knee, and wherein the second mounting member also includes spaced projecting connector link portions adapted to extend upward adjacent the wearer's knee, with adjacent ends of each resultant pair of the connector link portions pivotably interconnected for limited movement by one of the hinges. Further, each stop plate member and lug plate member has a circular periphery and the circumferentially extending track in the stop plate member and the lug on the lug plate member are located at their respective peripheries. The projecting lug on each lug plate member is integral therewith and also is received in a slot in its respective mounting member to prevent relative movement between the lug plate member and the mounting member. First and second retaining members, each having a noncircular hub receivable in correspondingly shaped-apertures in respective ones of the lug and stop plate members, and in the mounting members, are provided for preventing rotation of the plate members relative to their respective mounting members, with a securing mechanism securing the retaining members together so as to permit relative rotation therebetween. For this purpose, the securing mechanism includes a securing screw extending through one of the retaining members and screwthreadably received in the other retaining member, with a set screw in the latter retaining member limiting the degree of screw-threaded movement of the securing screw into that retaining member, to prevent the retaining members from being clamped together against relative rotational movement by the securing screw.

Each hinge also comprises a third plate member adapted to be secured to one of the projecting connector link portions of one of the upper mounting members for movement therewith, by one of the retaining members, so that the lug, stop and third plate members of the hinge are arranged in coaxial relationship with the projecting connector link portions of the associated mounting members disposed between respective ones of the plate members, and with the lug, stop and third plate members defining inner, intermediate and outer plate members, respectively. The mounting members may be formed of a molded, interlaced unidirectional tape material, and the upper mounting member also may include a support member having one end secured thereto and having an opposite free end adapted to be inserted in a pocket of clothing of the wearer, for supporting the knee brace assembly on the wearer.

BRIEF DESCRIPTION OF THE DRAWINGS

FIG. 5 is an enlarged, isometric exploded view of a hinged connection; and

FIG. 6 is an enlarged cross-sectional view of a hinged connection, taken along the line 6—6 in FIG. 1.

DETAILED DESCRIPTION

Figure 1:
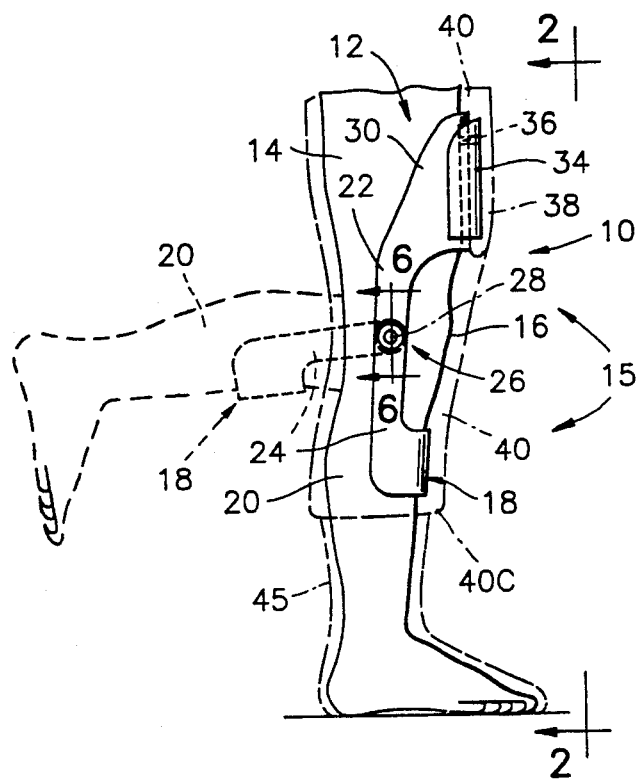
FIG. 1 is a side elevational view of a hinged knee brace assembly in accordance with the invention, mounted on a wearer's leg.
Figure 2:
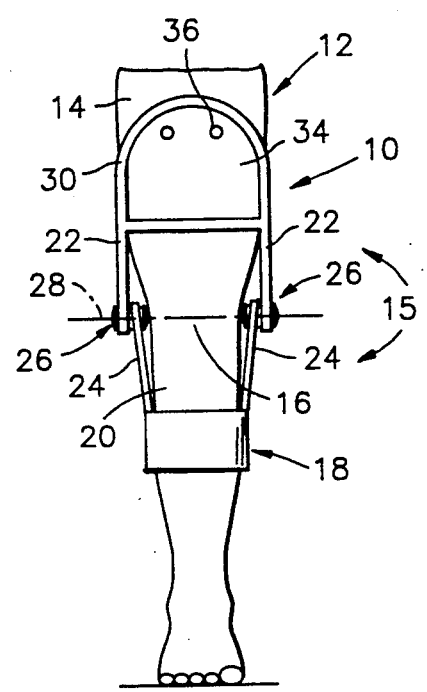
FIG. 2 is a front elevational view as seen along the line 2—2 in FIG. 1.

Referring to FIGS. 1 and 2, a hinged knee brace assembly 10 in accordance with the subject invention includes an upper cuff or first mounting member 12 which is adapted to be mounted on a thigh or upper leg portion 14 of a wearer's leg 15 above the wearer's knee 16, and a lower cuff or second mounting member 18 which is adapted to be mounted on a calf or lower leg portion 20 of the wearer below the knee. The upper mounting member 12 includes a pair of spaced downwardly projecting integral connector link portions 22, and the lower mounting member 18 includes a pair of spaced upwardly projecting integral connector link portions 24, which define pairs of the connector link portions on opposite sides of the knee 16. Adjacent ends of the resultant pairs of the connector link portions 22 and 24 are pivotably interconnected for limited movement by respective hinges 26 located on opposite sides of the knee 16 at a transverse bending axis 28 of the knee. More specifically, the hinges 26 permit normal flexing of the knee 16, such as bending of the calf 20 of the wearer rearward or clockwise relative to the wearer's thigh 14, as viewed in FIG. 1, for example, from a solid line position into a broken line position as illustrated in that figure. However, the hinges 26 prevent unnatural counter clockwise bending of the wearer's calf 20 forward from the solid line position in FIG. 1, which could cause serious injury and/or possible permanent ligament, cartilage or other damage to the knee 16.

Figure 3:
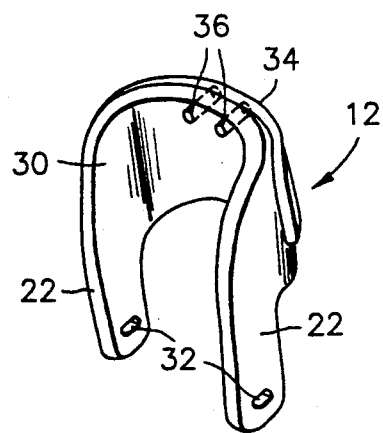
FIG. 3 is an enlarged isometric view of an upper cuff mounting member of the hinged knee brace assembly.

Referring to FIG. 3, the upper mounting member 12 includes an upper cuff portion 30 of generally semi-circular configuration, from which the connector link portions 22 depend. Lower ends of the connector link portions 22 include noncircular retaining member-receiving apertures 32 of essentially elliptical cross section. Further, an arcuate-shaped support member 34 is secured adjacent an upper edge to an outer surface of the semi-circular portion 30 of the upper mounting member 12 by a pair of rivets 36, with a lower edge portion of the support member being free and unconnected to the mounting member, so that the support member can be inserted in a suitable pocket 38 of clothing 40 (e.g., athletic uniform) illustrated in phantom in FIG. 1, for supporting the upper mounting member, and thus the lower mounting member 18 and the hinges 26, on the wearer's leg 15. The upper mounting member 12 also may be otherwise supported on the wearer's leg 15 by suitable strapping (not shown), and may be provided with a suitable padded lining, not shown.

Figure 4:
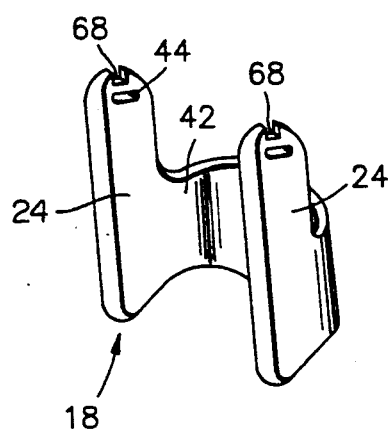
FIG. 4 is an enlarged isometric view of a lower cuff mounting member of the hinged knee brace assembly.

Referring to FIG. 4, the lower mounting member 18 is of similar construction to the upper mounting member 12, and comprises a lower semi-circular cuff portion 42 from which the upstanding connector link portions 24 extend. Similarly, upper ends of the connector link portions 24 are provided with noncircular retaining member-receiving apertures 44 of essentially elliptical cross section. In addition to the support provided by the upper mounting member 12 on the wearer's leg 15, the lower mounting member 18 also may otherwise be supported on the wearer's leg by suitable strapping (not shown), a tight-fitting cuff 40C of the wearer's uniform 40, a tight-fitting sock 45, etc.

As is best shown in FIG. 5, each hinge 21 includes an essentially circular stop plate member 46, a lug plate member 48, and an outer plate member 50. When assembled, the stop plate 46 and the lug plate 48 receive an upper end portion of the associated lower mounting member connector link portion 24 therebetween, and the stop plate and the outer plate 50 receive the adjacent lower end of the associated upper mounting member connector link portion 22 therebetween. To provide lateral stability and reinforcement to the knee brace assembly 10, the stop, lug and outer plate members 46, 48 and 50 have a relatively large diameter as compared to the heads of a normal connector pin or rivet, such as on the order of 2", with a thickness on the order of 1/16". In this connection, in the disclosed embodiment of the invention, the hinge 26 further includes an inner retaining member 52, an outer retaining member 54, a securing screw 56, and a set screw stop 58 for limiting screw-threaded movement of the securing screw, with the retaining members having circular, smooth-surfaced and dome-shaped head portions which as is clearly shown in FIG. 6, have a relatively small diameter as compared to the stop, lug and outer plate members 46, 48 and 50.

More specifically, a peripheral portion of the stop plate 46, having an arc on the order of 18-0° degrees, is recessed with respect to the remainder of the periphery of the stop plate, to define a circumferentially extending track 60 having radially extending stop surfaces 62 and 64 at its opposite ends. Further, a circular periphery of the lug plate 48 includes an integral laterally projecting lug 66 which is receivable in a slot 68 in the upper end of the adjacent connector link portion 24 to prevent relative movement between the lug plate and the connector link portion. The lug 66, which preferably extends along an arc on the order of 30° to provide necessary lateral bending strength, further projects beyond the slot 68 in the connector link portion 24 closely adjacent the track 60 of the stop plate 46. Thus, as the stop plate 46 and lug plate 48 rotate relative to one another, the lug 66 can travel in the track 60 and selectively engage one or the other of the radially extending stop surfaces 62 or 64, to limit the relative rotational movement of the stop and lug plates to an arc on the order of 150°.

In this connection, when the upper and lower leg portions 14 and 20 of the wearer are in a straight-line relationship as illustrated in FIG. 1, the lug 66 is essentially engaged against the uppermost stop surface 62 as viewed in FIG. 5, to prevent detrimental bending of the wearer's knee 15 counterclockwise in FIG. 1, into an unnatural position, as above described. At the same time, due to the ability of the lug 66 to travel along the track 60, the wearer's knee 15 can be bent in an opposite direction into various natural positions, as illustrated in broken lines in FIG. 1, by way of example, with the lug 66 engaging the lowermost radially-extending stop surface 64 of the stop plate 46 to prevent excessive hyperextension and injury to the wearer's knee 15 when it is bent in that direction. Further, while in the disclosed embodiment of the invention the stop surfaces 62 and 64 are shown spaced 180° degrees apart, it is apparent that lesser spacings can be used to provide a more restrictive degree of knee bending movement, as may be desired.

In addition to the lug plate 48 being received in the slot 68 in the lower mounting member connector link portion 24 to prevent relative movement therebetween, relative movement between the lug plate and the connector link portion further is prevented by the inner retaining member 52. For this purpose, the inner retaining member 52 includes an unthreaded through passageway 69, and a projecting hub portion 70 of noncircular configuration, in this instance having a cross section of an essentially elliptical shape with flat longitudinally extending upper and lower sides 72, curved opposite ends 74 and a flat vertical surface 76. The hub 70 is received in a correspondingly-shaped aperture 78 in the lug plate 48 and the aperture 44 in the connector link portion 24, which also is of the same shape, to prevent relative movement therebetween.

Similarly, relative movement between the stop plate 46, the outer plate 50 and the upper mounting member connector link portion 22 disposed therebetween, is prevented by the outer retaining member 54, which includes a screw-threaded through passageway 79 and also includes a projecting hub portion 80 having a cross section of the same essentially elliptical shape as the hub 70, with flat longitudinally extending upper and lower sides 82, curved opposite ends 84 and a flat vertical surface 86, and receivable in correspondingly-shaped apertures 88 and 90 in the stop plate 46 and outer plate 50, respectively, and in the aperture 32 (of the same shape) in the connector link portion 22.

Referring to FIG. 6, when the stop, lug and outer plates 46, 48 and 50, connector link portions 22 and 24, and retaining members 52 and 54, are assembled together as shown in this Figure, they are retained in assembled relationship by the securing screw 56 which extends through the unthreaded passageway 69 in the inner retaining member 52 and is screw-threaded into the passageway 79 in the hub 80 of the outer retaining member 54. The screw-threaded movement of the securing screw 56 into the second retaining member hub 80 is limited so that the flat opposed vertical surfaces 76 and 86 of the retaining member hubs 70 and 80 are not clamped into firm engagement with one another, so as to prevent the desired free relative movement between the subassembly formed by the lower mounting member connector link portion 24, lug plate 48 and inner retaining member 52, on the one hand, and the subassembly comprising the upper mounting member connector link portion 22, stop plate 46, outer plate 50 and outer retaining member 54, on the other hand. For this purpose, the set screw stop 58 is screw-threaded into the passageway 79 in the outer retaining member 54 a necessary desired amount so as to limit the screw-threaded movement of the securing screw 56 into the outer retaining member, thereby preventing excessive tightening of the retaining members 52 and 54 together.

Preferably, the upper and lower mounting members 12 and 18 are formed of material having high strength and impact resistance, with at least same degree of limited flexibility, such as a molded interlaced unidirectional tape material as disclosed in co-pending U.S. patent application Ser. No. 07/130,854, filed Dec. 9, 1987, in the names of Paul T. Craven, et al., and entitled MULTI-DIRECTIONAL, LIGHT-WEIGHT, HIGH-STRENGTH INTERLACED MATERIAL AND METHOD OF MAKING THE MATERIAL, which application is assigned to the same Assignee as the subject application. More specifically, the material may be that formed from interlaced tapes comprising unidirectional carbon fibers impregnated with a thermoplastic and then subjected to a molding operation as disclosed in the co-pending application. In the alternative, the upper and lower mounting members 12 and 18 may be formed of other types of molded plastic material. Similarly, the support member 34 may be formed of a similar molded interlaced unidirectional tape material, or of another suitable plastic material. Further, the various parts of the hinges 26 preferably are formed of a noncorrosive metal, such as stainless steel.

In summary, a new and improved hinged knee brace assembly 10, which includes a new and improved hinge 26, is of simple, compact and rugged construction, and is easy to assemble and mount on a wearer, has been disclosed. For example, relative movement between each lug plate 48 and its associated lower mounting member connector link portion 24 is readily and effectively prevented by the lug 66 on the lug plate being received in the slot 68 in the connector link portion, and by the hub 70 of the inner retaining member 52 being received in the corresponding apertures 78 and 44 in the lug plate and connector link portion, respectively. Similarly, relative rotation is readily and effectively prevented between each stop plate 46, and its associated upper mounting member connector link portion 22 and outer plate 50, by the hub 80 of the outer retaining member 54 extending through the correspondingly-shaped apertures 88, 32 and 90, respectively, in these parts. The resultant subassemblies then are held together so as to permit relative movement therebetween, by the securing screw 56, with the set screw stop 58 in the outer retaining member 54 being adjustable to limit the screw-threaded movement of the securing screw, so as to ensure against over-tightening thereof. The upper mounting member 12 also is provided with the support member 34 which is receivable in the pocket 38 of the wearer's clothing 40 (e.g., uniform) to facilitate mounting and retention of the knee brace assembly 10 on the wearer.

We claim:

1. A hinge for use with a knee brace assembly wherein the assembly comprises first and second mounting means for mounting the assembly to a wearer's leg above and below a wearer's knee, respectively, the hinge comprising:

a stop plate member adapted to be connected to one of the mounting means for movement therewith;

a lug plate member adapted to be connected to the other of the mounting means for movement therewith;

a third plate member adapted to be secured to one of the first and second mounting means for movement therewith, said lug, stop and third plate members being adapted to be arranged in coaxial relationship with portions of said first and second mounting means disposed between respective ones of said plate members so that said plate members provide lateral stability and reinforcement to said portions;

pivot means for pivotably interconnecting the connected stop plate member-and-one mounting means, to the connected lug plate member-andother mounting means, for relative pivotable movement, the pivot means including first and second retaining members each having noncircular hub portions receivable in correspondingly-shaped apertures in respective ones of the plate members and their respective mounting means, for preventing rotation of said plate members relative to their respective mounting means; and means for securing the first and second retaining members together so as to permit relative rotation therebetween;

the stop plate member including a circumferentially extending track having stop surfaces at opposite ends thereof, and the lug plate member including projecting lug means receivable in the circumferentially extending track and selectively engageable with at least one of the stop surfaces for limiting said relative pivotable movement between said connected plate members-and-mounting means.

2. The hinge as recited in claim 1, wherein the stop plate member has an essentially circular periphery and the track therein is at said periphery.

3. The hinge as recited in claim 2, wherein the lug plate member also has an essentially circular periphery and the projecting lug means is located at said periphery.

4. The hinge as recited in claim 3, wherein the projecting lug means is integrally formed with said lug plate member.

5. The hinge as recited in claim 1, wherein the projecting lug means is adapted to be received in a slot in said other mounting means to prevent relative movement between said lug plate member and said other mounting means.

6. The hinge as recited in claim 1, wherein:
the securing means includes a securing screw extending through one of the retaining members and screw-threadably received in the other retaining member; and
adjustable movement-limiting means is provided for limiting the degree of screw-threaded movement of said securing screw into said other retaining member, to prevent clamping of said retaining members together against relative rotational movement by said securing screw.

7. The hinge as recited in claim 6, wherein the adjustable movement-limiting means is a set screw threadably received in said other retaining member.

8. The hinge as recited in claim 1, wherein:
the stop plate member has an essentially circular periphery and the track therein is at said periphery;
the lug plate member also has an essentially circular periphery and the projecting lug means is integrally formed with said lug plate member at said periphery, said projecting lug means being adapted to be received in a slot in said other mounting means to prevent relative movement between said lug plate member and said other mounting means;
the lug, stop and third plate members are adapted to be located between the first and second retaining members;
the lug and stop plate members are adapted to be located on opposite sides of said portion of one of the first and second mounting means;
the third plate member is adapted to be located between one of the retaining members and said portion of the other of the first and second mounting means, and includes an aperture which receives the hub portion of the retaining member therethrough so that the third plate member is movable with the one retaining member, said lug, stop and third plate members being of larger diameter than said retaining members to provide said lateral stability and reinforcement to said portions of said first and second mounting means;
the securing means includes a securing screw extending through one of the retaining members and screw-threadably received in the other retaining member; and
adjustable movement-limiting means is provided for limiting the degree of screw-threaded movement of said securing screw into said other retaining member, to prevent clamping of said retaining members together against relative rotational movement by said securing screw.

9. The hinge as recited in claim 8, wherein the adjustable movement limiting means is a set screw threadably received in said other retaining member.

10. A knee brace assembly, which comprises:
first mounting means for at least partially encompassing an upper leg portion of a wearer above the wearer's knee, said first mounting means including spaced projecting connector link portions adapted to extend downward adjacent opposite sides of the wearer's knee;
second mounting means for at least partially encompassing a lower leg portion of the wearer below the wearer's knee, said second mounting means including spaced projecting connector link portions adapted to extend upward adjacent opposite sides of the wearer's knee; and
first and second hinge means for interconnecting respective pairs of said spaced projecting connector link portions of said first and second mounting means for limited pivotable movement;
each of said hinge means including a stop plate member and a lug plate member connected to respective ones of said mounting means for movement therewith, to define plate member-mounting means for movement therewith, to define plate member-mounting means subassemblies, said stop plate member including a circumferentially extending track having stop surfaces at opposite ends thereof, and said lug plate member including projecting lug means received in the circumferentially extending track and selectively engageable with at least one of the stop surfaces for limiting relative movement between the plate member-and-mounting means subassemblies;
each of said hinge means comprising a third plate member adapted to be secured to one of the projecting connector link portions of one of the mounting means for movement therewith, and said lug, stop and third plate members of each hinge means being in coaxial relationship with said projecting connector link portions of said first and second mounting means disposed between respective ones of said plate members so that said plate members provide lateral stability and reinforcement to said connector link portions; and
each of said hinge means further comprising first and second retaining members having noncircular hub portions receivable in correspondingly-shaped apertures in respective ones of the plate members and the mounting means, for preventing rotation of said plate members relative to their respective mounting means; and means for securing the first and second retaining members together so as to permit relative rotation therebetween.

11. The knee brace assembly as recited in claim 10, wherein each hinge means stop plate member has an essentially circular periphery and the track therein is at said periphery.

12. The knee brace assembly as recited in claim 11, wherein each hinge means lug plate member also has an essentially circular periphery and the projecting lug means thereof is located at said periphery.

13. The knee brace assembly as recited in claim 12, wherein each projecting lug means is integrally formed with its respective lug plate member.

14. The knee brace assembly as recited in claim 10, wherein the projecting lug means of each lug plate member is received in a slot in its respective mounting means to prevent relative movement between said lug plate member and said mounting means.

15. The knee brace assembly as recited in claim 10, wherein the securing means includes:
 a securing screw extending through one of the retaining members and screw-threadably received in the other retaining member; and
 adjustable means for limiting the degree of screw-threaded movement of said securing screw into said other retaining member, to prevent said retaining members from being clamped together against relative rotational movement by said securing screw.

16. The knee brace assembly as recited in claim 15, wherein the adjustable movement-limiting means is a set screw threadably received in said other retaining member.

17. The knee brace assembly as recited in claim 10, wherein said first and second mounting means are formed of a molded interlaced unidirectional tape material.

18. The knee brace assembly as recited in claim 10, which further comprises:
 a support member having one end secured to said first mounting means and having an opposite free end adapted to be inserted in a pocket of clothing of the wearer, to support the knee brace assembly on the wearer.

19. The knee brace assembly as recited in claim 10, wherein:
 each hinge means stop plate member has an essentially circular periphery and the track therein is at said periphery;
 each hinge means lug plate member also has an essentially circular periphery and the projecting lug means thereof is integrally formed with said lug plate member at said periphery, with said projecting lug means also being received in a slot in its respective mounting means to prevent relative movement between said lug plate member and said mounting means;
 the lug, stop and third plate members of each hinge means are located between the first and second retaining members thereof:
 the lug and stop plate members of each hinge means are located on the opposite sides of one of the respective mounting means;
 the third plate member of each hinge means is located between one of the hinge means retaining members and the other of the respective mounting means, and includes an aperture which receives the hub portion of the one retaining member therethrough so that the third plate member is movable with the one retaining member, and said lug, stop and plate members are of larger diameter than said retaining members to provide said lateral stability and reinforcement of the connector link portions;
 each hinge means includes a securing screw extending through one of the retaining members and screw-threaded into the other retaining member;
 adjustable movement-limiting means is provided for limiting the screw-threaded movement of said securing into said other retaining member, to prevent said retaining members from being clamped together against relative rotational movement by said securing screw; and
 said first and second mounting means are formed of a molded interlaced unidirectional tape material.

20. The knee brace assembly as recited in claim 19, wherein the adjustable movement limiting means of each hinge means is a set screw threadably received in said other retaining members of the hinge means.

21. A hinge for use with a knee brace assembly wherein the assembly comprises first and second mounting means for mounting the assembly to a wearer's leg above and below a wearer's knee, respectively, the hinge comprising:
 a stop plate member adapted to be connected to one of the mounting means for movement therewith;
 a lug plate member adapted to be connected to the other of the mounting means for movement therewith;
 a third plate member adapted to be secured to one of the first and second mounting means for movement therewith, said lug, stop and third plate members being adapted to be arranged in coaxial relationship with portions of said first and second mounting means disposed between respective ones of said plate members so that said plate members provide lateral stability and reinforcement to said portions; and
 pivot means for pivotably interconnecting the connected stop plate member-and-one mounting means, to the connected lug plate member-and-other mounting means, for relative pivotable movement, the pivot means including first and second retaining members for retaining said lug, stop and third plate members in assembled relationship, said lug, stop and third plate members being of larger diameter than the retaining members to provide said lateral stability and reinforcement to said portions of said first and second mounting means; and
 the stop plate member including a circumferentially extending track having stop surfaces at opposite ends thereof, and the lug plate member including projecting lug means receivable in the circumferentially extending track and selectively engageable with at least one of the stop surfaces for limiting said relative pivotable movement between said connected plate members-and-mounting means.

22. A knee brace assembly, which comprises:
 first mounting means for at least partially encompassing an upper leg portion of a wearer above the wearer's knee, said first mounting means including spaced projecting connector link portions adapted to extend downward adjacent opposite sides of the wearer's knee;

second mounting means for at least partially encompassing a lower leg portion of the wearer below the wearer's knee, said second mounting means including spaced projecting connector link portions adapted to extend upward adjacent opposite sides of the wearer's knee; and first and second hinge means for interconnecting respective pair of said spaced projecting connector link portions of said first and second mounting means for limited pivotable movement;

each of said hinge means including a stop plate member and a lug plate member connected to respective ones of said mounting means for movement therewith, to define plate member-mounting means subassemblies, said stop plate member including a circumferentially extending track having stop surfaces at opposite ends thereof, and said lug plate member including projecting lug means received in the circumferentially extending track and selectively engageable with at least one of the stop surfaces for limiting relative movement between the plate member-and-mounting means subassemblies;

each of said hinge means comprising a third plate member adapted to be secured to one of the projecting connector link portions of one of the mounting means for movement therewith, and said lug, stop and third plate members of each hinge means being in coaxial relationship with said projecting connector link portions of said first and second mounting means disposed between respective ones of said plate members so that said plate members provide lateral stability and reinforcement to said connector link portions; and each of said hinge means further comprising first and second retaining members for retaining said lug, stop and third plate members in assembled relationship, said lug, stop and third plate members being of larger diameter than their respective retaining members to provide said lateral stability and reinforcement to said portions of said connector link portions.

* * * * *